United States Patent
Ledford et al.

(10) Patent No.: US 8,473,502 B2
(45) Date of Patent: Jun. 25, 2013

(54) INTERASSOCIATING DATA OF A MEDICAL DEVICE

(75) Inventors: Ricky L. Ledford, Little Canada, MN (US); Jessica Dawn Hagg, Maplewood, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 106 days.

(21) Appl. No.: 13/010,835

(22) Filed: Jan. 21, 2011

(65) Prior Publication Data

US 2012/0084303 A1 Apr. 5, 2012

Related U.S. Application Data

(60) Provisional application No. 61/388,964, filed on Oct. 1, 2010.

(51) Int. Cl.
*G06F 17/30* (2006.01)
(52) U.S. Cl.
USPC .......................................... 707/755; 604/500
(58) Field of Classification Search
USPC ............................ 340/635; 604/500; 707/755
See application file for complete search history.

(56) References Cited

U.S. PATENT DOCUMENTS

| | | |
|---|---|---|
| 2002/0193679 A1 | 12/2002 | Malave et al. |
| 2009/0150484 A1 | 6/2009 | Roberts |
| 2009/0156991 A1 | 6/2009 | Roberts |
| 2009/0270833 A1 | 10/2009 | DeBelser et al. |

FOREIGN PATENT DOCUMENTS

EP 1922984 A1 5/2008

OTHER PUBLICATIONS

International Search Report and Written Opinion from counterpart PCT Application No. PCT/US2011/043695 mailed on Feb. 23, 2012 (10 pages).

*Primary Examiner* — Huawen Peng
(74) *Attorney, Agent, or Firm* — Wood, Herron & Evans, LLP (57) ABSTRACT

Methods, a medical device, and a computing system configured to interassociate data of the medical device are provided. The medical device uses a processor to collect data and include a respective event set identifier with data developed in connection with activity starting with a respective identifiable event of the medical device. The data may thus be parsed based on the event set identifier to access data for an identifiable event.

42 Claims, 6 Drawing Sheets

INTERASSOCIATING DATA OF A MEDICAL DEVICE

CROSS-REFERENCE TO RELATED APPLICATION

This application claims the benefit of U.S. patent application No. 61/388,964 entitled "INTERASSOCIATING DATA OF A MEDICAL DEVICE" and filed on Oct. 1, 2010, which application is incorporated by reference in its entirety herein.

TECHNICAL FIELD

The present invention relates to medical devices, and more particularly to accessing data of a medical device.

BACKGROUND OF THE INVENTION

Many medical devices used in the treatment, diagnosis, or care of patients are adapted to collect, and/or transmit data to a computer. The data can include various details about the medical device and its performance. Clinicians and technicians may need to access some or all of the data collected by the medical device, such as from the medical device directly or from a computer to which the data has been transmitted. The clinician may use some or all of that data to facilitate the treatment, diagnosis, or care of the patient whereas the technician may use some of that data to monitor the status or performance of the device. In many situations, the computer may be a server which amasses the data received from a number of such devices.

In order to deal with the data received from a plurality of medical devices, each medical device is configured to include with the data it sends to the server an identifier which is unique to that medical device. That identifier can then be used by the server or another computer accessing the server to facilitate accessing the data in respect of a particular medical device of interest. In some situations, the data transmitted by a medical device may also have a time-stamp related to the time the data is collected at the medical device. The time-stamp can be used by the server, for example, to chronologically order the data, which can be helpful in situations where communications networks or other factors cause the data to arrive at or be stored out of chronological order by the server.

The clinicians and technicians accessing the data often need to have the data organized around certain events associated with the medical device. Some medical devices may collect and/or transmit certain data related to the status or performance of the medical device during a start-up period associated with the event of turning the medical device on. Some medical devices may collect and/or transmit such data as well as operational data in relation to a selected event, such as in connection with patient monitoring or medication infusion. By way of example, a medical pump may be programmed to begin collecting and/or transmitting certain status data after it is turned on, and to continue to collect and/or transmit status data or the like for so long as the medical pump remains on. Once a new event is selected, such as an infusion regimen, the medical pump will begin to collect and/or transmit other data related to that infusion regimen, such as the details of the selected programming for that infusion regimen, progress of the infusion regimen, and behavior of the medical pump during the infusion regimen.

The data associated with those different events serves different, although sometimes overlapping, purposes from the different perspectives of the clinician and the technician. But to focus in on the desired information, it may be necessary that the data be parsed to find the start and stop times associated with the event so as to locate the data of interest in relation to the event. Such an approach is time consuming, complex, and possibly prone to error.

SUMMARY OF THE INVENTION

The present invention provides a mechanism for simply and automatically parsing data from a medical device in accordance with identifiable events of the medical device. To that end, and in accordance with the principles of the present invention, the medical device associates an event set identifier with the data for activity starting with an identifiable event. As a result, the data in regard to activity starting with an identifiable event is interassociated into an identifiable set of data based on the event set identifier. When data for a medical device is to be accessed, it can be readily parsed based on the event set identifier without the need to find start and/or stop times, for example, in order to access the desired data for an identifiable event. To that end, all of the data having a common event set identifier can be readily identified such that the data for an identifiable event can be readily accessed and made available to the clinician or technician. Advantageously, the data for one or more medical devices is parsed electronically using a processor to select or group the data into one or more sets based on the event set identifier(s).

The event set identifier can be associated with the pertinent data as it is collected by the medical device, such that the data related to activity starting with an identifiable event can be accessed at the medical device or via a computer communicating with the medical device. Further, data transmitted to a computer such as a server, for example, can include the applicable event set identifier such that the data for an identifiable event can be accessed, or the data for multiple identifiable events can be easily grouped by event set identifier, such as in one or more reports obtained by accessing the data.

The event set identifier can be a number which is incremented, decremented, or otherwise adjusted upon either the initiation or the conclusion of an identifiable event. Thus, by way of example, when the medical device is turned on, the previous event set identifier may be incremented to thus apply that new event set identifier to the data being collected and/or transmitted by the medical device going forward until the next identifiable event. If the medical device is a medical pump, for example, when the clinician selects an infusion regimen, such as by beginning the programming steps therefor or confirming the settings thereof, that will cause the event set identifier to be incremented. Incrementing the event set identifier thus creates yet another new event set identifier, which will now be provided with the data going forward such that the programming activity, medical pump activity, and related alarms, if any, in regard to the infusion regimen will be associated with that event set identifier. As a result, the data for that medical device can be easily parsed, such as later at the server, to locate the data for activity starting with that identifiable event. Alternatively, the event set identifier could be decremented, rather than incremented, at each identifiable event. Alternatively or additionally, the event set identifier could be incremented (or decremented) at the end of an identifiable event, one example of which could be the end of an infusion regimen where the medical device is a medical pump. In that situation, the end of an infusion regimen could be determined by detecting that the volume infused has reached the programmed value, or detecting that the medicament supply container (such as a cassette or syringe) is empty.

As a result, there is no need for the server or anyone accessing the data for a medical device to undertake the time or devote the resources to parsing the data in order to locate the data of interest. Instead, the event set identifier can be used to access a set or sets of data associated with an identifiable event or events.

By virtue of the foregoing, there is thus provided a mechanism for simply and automatically parsing data from a medical device in accordance with identifiable events of the device. These and other advantages of the present invention shall be made apparent from the accompanying drawings and detailed description thereof.

BRIEF DESCRIPTION OF THE DRAWINGS

The accompanying drawings, which are incorporated in and constitute a part of this specification, illustrate aspects of the present invention and, together with a general description of the invention given above and the detailed description of the invention given below, serve to explain the principles of the invention.

DETAILED DESCRIPTION OF THE DRAWINGS

Figure 1:
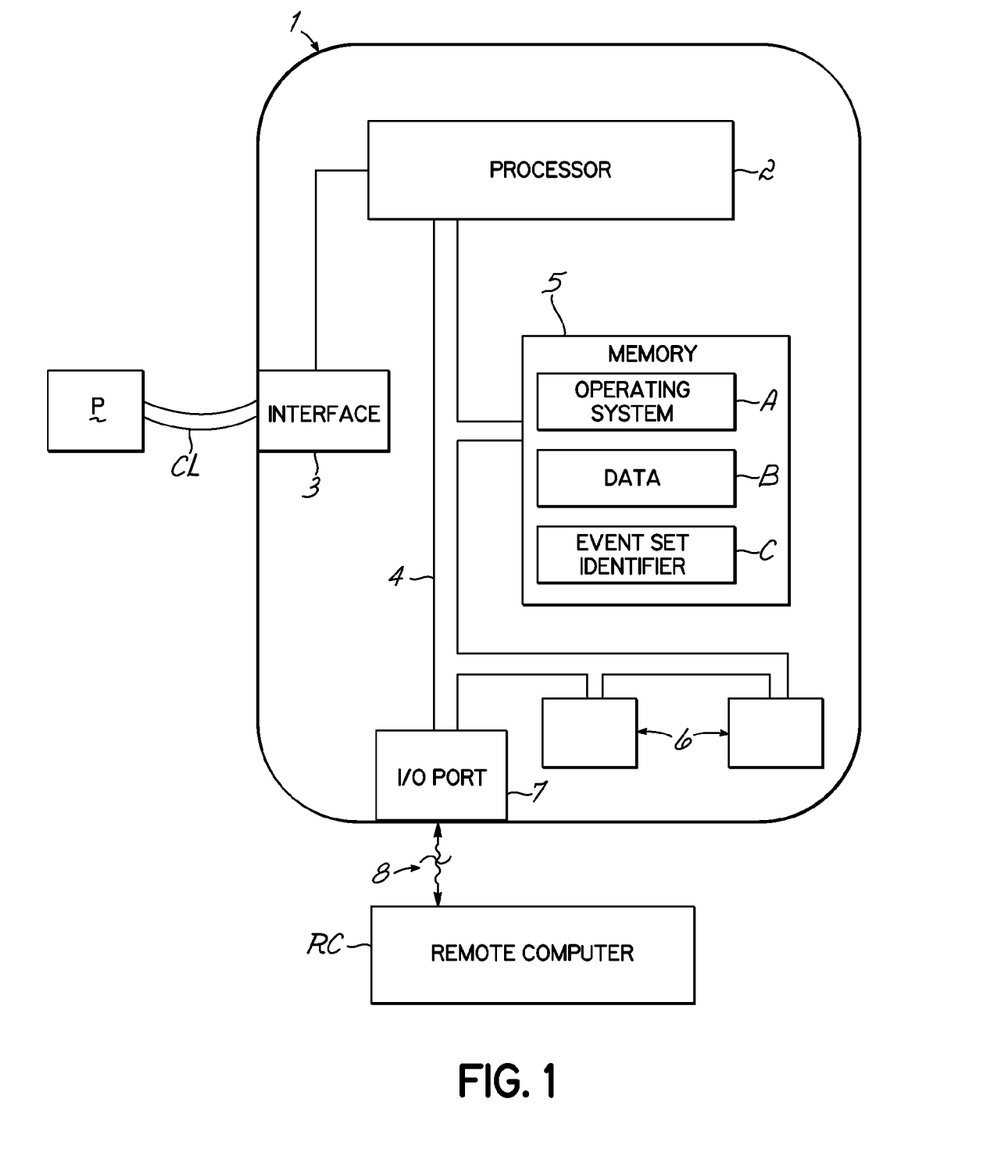
FIG. 1 is a diagrammatic view of a medical device configured to interassociate data with respect to activity starting with an identifiable event in accordance with the principles of the present invention.

With reference to FIG. 1 there is shown a block diagram of an exemplary medical device 1, configured with an embodiment of an event set identifier feature for purposes of explaining the principles of the present invention. To that end, medical device 1 is adapted to operatively interact with a patient P, such as via a coupling line CL. Coupling line CL may be an electronic cable for monitoring the patient P or may be a fluid line for infusion fluid into the patient P, by way of examples. Medical device 1 also includes a processor 2 which operatively controls an interface 3 with the coupling line CL (such as to obtain data from patient P and/or cause fluid to expel into coupling line CL, depending upon the type of medical device 1). Medical device 1 also includes a bus 4 coupled between processor 2 and a memory 5, operator control switches 6, and I/O port 7. Memory 5 includes, for example, the operating software A for processor 2, data B data reflecting status and performance data collected by medical device 1, and an event set identifier C, for purposes to be described.

As medical device 1 operates, various identifiable events will typically occur. By way of example, a user (not shown) such as a clinician or patient may actuate a switch 6 causing medical device 1 to turn on. When that occurs, processor 2 detects that turn-on event and adjusts the value of an event set identifier C stored in memory 5 to define a new event set identifier C. Thereafter, as data is collected by medical device 1 reflecting, for example, the status and condition of medical device 1 and/or other activity thereof, that data B is stored in memory 5 and associated with the event set identifier C. When another identifiable event is detected, such as when a user actuates another switch or switches 6 to program and/or start a procedure (such as patient monitoring or fluid infusion depending on the type of medical device 1), the value of the event set identifier C is adjusted by processor 2 to define a new, current event set identifier C. Thereafter, as the procedure is set up, implemented, and operated, and possibly thereafter until a yet further identifiable event is detected by processor 2, data for the various activity is collected by medical device 1, which may now also include performance of medical device 1 as well as data related to activity of interface 3 and/or processor 2, for example. That data B is stored in memory 5 and associated with the current event set identifier C.

As a consequence, data in regard to activity starting with an identifiable event is interassociated into an identifiable set based on the event set identifier. Thus, memory 5 may be accessed, such as via I/O port 7 and the data B parsed with processor 2 to obtain one or more sets of data for respective identifiable events.

Alternatively or additionally, the data B, along with its respective event set identifier C, may be transmitted, either as it is collected or in blocks, to a remote computer RC (such as a bedside computer, a clinician's computer, a hospital computer, or the like) via I/O port 7 either directly or over a wired or wireless network as at 8 (in which event, I/O port 7 may include the necessary electronics to support such communications). The data can then be stored and/or manipulated through the computer RC. When the data is to be accessed, it can be parsed, such as by the remote computer RC, so as to collect and/or report a set (or sets) of data interassociated by a common event set identifier for that data (or, as to each set of multiple sets of data, their respective common event set identifier for that set of data).

While memory 5 is shown as a single component, it will be appreciated that memory 5 could be comprised of multiple components coupled such as via bus 4, and can include registers (not shown) associated with processor 2 and different forms of memory components. Further, while data B and event set identifier C are shown as being stored separately in memory 5, they could be stored together in memory 5. Further, medical device 1 could include a display (not shown) to provide information to the user, and one or more of operator control switches could be soft keys interactive with the display and/or changeable in their function depending upon the particular event or state of the medical device 1.

At the beginning (or at the end) of an identifiable event, the previous value of the event set identifier C is adjusted, such as by incrementing or decrementing the value by one for example, to define a new value for event set identifier C. Alternatively, the event set identifier could have various fields, one for example indicating the type of event, and another indicating how many times that event has been initiated (or ended) so as to thus adjust the prior, and thereby define the new, event set identifier.

Figure 2:
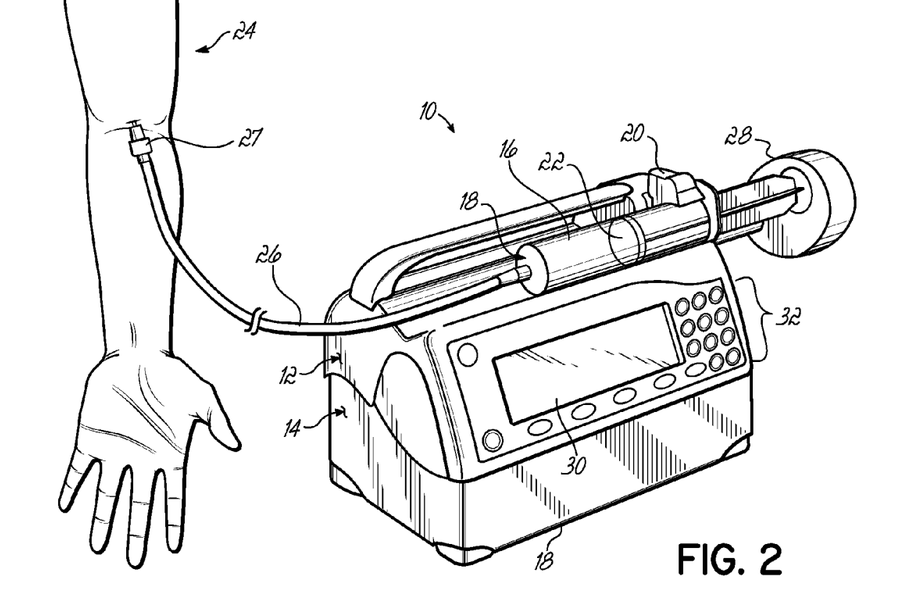
FIG. 2 is a perspective illustration of an exemplary medical device in the form of a syringe pump configured to interassociate data with respect to activity starting with an identifiable event for purposes of explaining the principles of the invention.

One particular embodiment of the event set identifier feature of the present invention is implemented in a medical device 1 in the form of a syringe pump 10. The syringe pump 10 includes a head 12 and a base 14. As illustrated in FIG. 2, the syringe pump 10 is configured to infuse the fluid contents of a syringe 16 via a coupling line CL in the form of a fluid line 26 coupled to a patient's arm 24 such as through a catheter 27. Syringe 16 includes a barrel 18 supported on the head 12 of the syringe pump 10 and secured by a clamp 20. The clamp 20 is coupled to a sensor 61 (FIG. 2), which is typically internal to the head 12, to determine the outer diameter of the syringe 16. The syringe 16 includes a plunger 22 moveable within the barrel 18 to expel the fluid contents into the fluid line 26.

To this end, a stepper motor 58 (FIG. 3) internal to the housing head 12 actuates a piston drive 28 to move the plunger 22. A sensor 61 (FIG. 3) monitors the force exerted by the piston drive 28 to determine the fluid force of the fluid upon the patient 24. The piston drive 28 drives the fluid out of the syringe 16 at a controlled rate based on parameters programmed into the syringe pump 10 including certain parameters related to the physical characteristics of the syringe 16. The barrel 18 of the syringe 16 is retained so as to allow the plunger 22 to be pushed by the piston drive 28 such as by means of a slot to hold at least a portion of the barrel 18. The plunger 22 may be retained by a forward facing surface of the piston drive 28 that clamps the base of the plunger 22 thereto.

As illustrated in FIG. 2, the head 12 includes a display 30 and an operator interface 32 comprised of a plurality of switches or the like. The display 30 may display options for a clinician (not shown) to choose through the operator interface 32. Input from the clinician may include actuating a switch of interface 32 to turn syringe pump 10 on, utilizing various aspects of interface 32 to select menu items such as programs and/or profiles, as well as data pertaining to characteristics of an infusion procedure, and utilizing various aspects of interface 32 to enter data.

Figure 3:
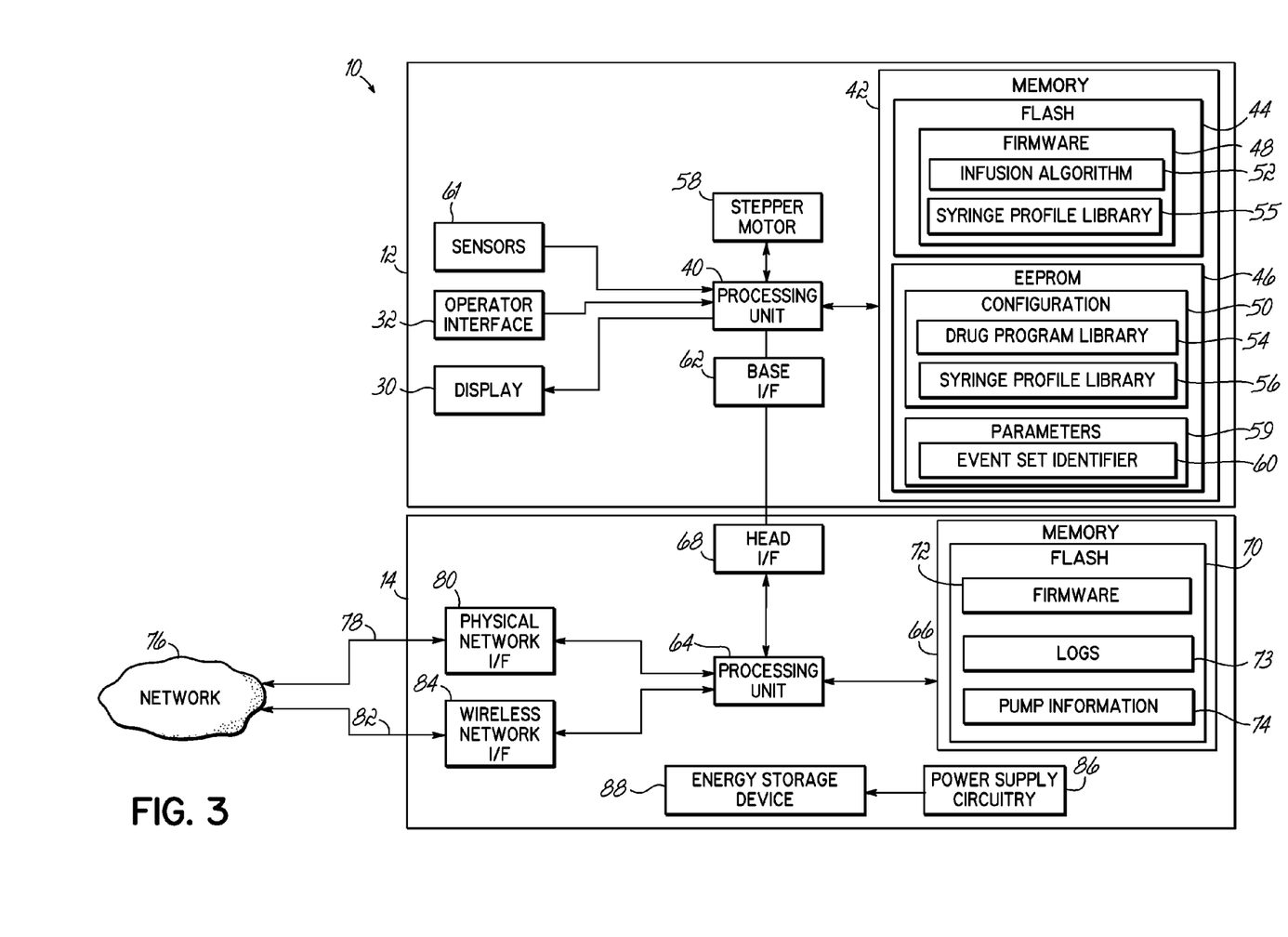
FIG. 3 is a diagrammatic illustration of the hardware and software components of the syringe pump of FIG. 2.

FIG. 3 illustrates a hardware and software environment for the syringe pump 10, and particularly the head 12 and base 14 thereof. The head 12 includes at least one head processing unit 40 coupled to a head memory 42. Each head processing unit 40 is typically implemented in hardware using circuit logic disposed in one or more physical integrated circuit devices, or chips. Each head processing unit 40 may be one or more microprocessors, micro-controllers, field programmable gate arrays, or ASICs, while head memory 42 may include a plurality of types of memory, including a flash memory 44 and an electronically erasable programmable read-only memory 46 (illustrated as, and hereinafter, "EEPROM" 46). As such, head memory 42 may be considered to include memory storage physically located elsewhere in the head 12 (e.g., any cache memory in the at least one head processing unit 40, as well as flash memory 44, EEPROM 46, and any additional memory in the head 12). Similarly, head memory 42, flash memory 44, and EEPROM 46 are also typically implemented using circuit logic disposed on one or more physical integrated circuit devices, or chips.

As illustrated in FIG. 3, the flash memory 44 is configured to contain firmware 48 for the head 12 while the EEPROM 46 is configured to contain configuration data 50. The firmware 48 includes data to control the components of the head 12 as well as an infusion algorithm 52. The infusion algorithm 52 is executed by the head processing unit 40 to determine a distance to move the plunger 22 of the syringe 16 over a time to achieve a desired rate or rates at which fluid is to be expelled from the syringe 16. By way of example, the distance-over-time to move the piston drive 28 to achieve a desired rate may be determined with respect to a drug program selected from at least one drug program library 54 in the configuration data 50, a syringe profile selected from at least one syringe profile library 55 in the firmware 48, a syringe profile selected from at least one syringe profile library 56 in the configuration data 50, and/or data input by the clinician through operator interface 32. Utilizing the foregoing, the head processing unit 40 determines the necessary commands to operate the stepper motor 58 to control the piston drive 28 coupled to thereto in a manner to expel the appropriate amount of fluid from the syringe 16 to perform a desired infusion regimen. The EEPROM 46 may also include a parameters section 59 that stores parameters associated with the syringe pump 10, and in particular an event set identifier 60 that is used to interassociate data with respect to activity starting with an identifiable event.

The head processing unit 40 is further coupled to the display 30 and the operator interface 32, as well as to a plurality of sensors 61. The plurality of sensors 61 may include any or all of a force transducer sensor to indicate the force exerted on the plunger 22 of a syringe 16, a syringe plunger loaded sensor to indicate that the plunger 22 of the syringe 16 is loaded on the piston drive 28, a plunger travel sensor to indicate the distance traveled by the plunger 22 of the syringe 16, a syringe size sensor coupled to the clamp 20 to indicate the size of the syringe 16, and a motor rotation sensor to indicate rotation of the stepper motor 58 and the amount thereof. The head processing unit 40 is coupled to a base interface 62 (illustrated as "base I/F" 62) to interface with the base 14.

With respect to the drug program library 54, each drug program therein is associated with custom infusion parameters which contain specific information about modes of operation used in the syringe pump 10, are associated with specific syringe profiles, and are used by the head processing unit 40 to determine how to operate the stepper motor 58 and piston drive 28 to infuse the fluid contents of the syringe 16. By way of example, a drug program may include a name that specifies the particular fluid that is to be infused by that drug program, the particular syringe profile to use with that drug program, as well as the mode of infusion to use in the procedure for expelling that particular fluid. The modes of infusion may include a continuous mode (a continuous infusion of a specific flow rate in ml/hr with regard to volume limits, loading dose or bolus dose, the bolus dose being an optional parameter to specify a bolus volume to be delivered over a specified time, the loading dose being an optional parameter to use a specified volume as a one-time-only bolus prior to the start of normal delivery, and the volume limit being an optional parameter in which the pump stops or enters a "Keep Vein Open" rate once a specified volume has been reached), a body weight infusion mode (that may be programmed by drug concentration, patient weight or drug dosage, in which the pump calculates the correct flow rate in ml/hr to achieve a specified drug dose with regard to volume limit, loading dose or bolus dose), a volume-over-time infusion mode (in which the pump calculates the flow rate for a dose volume over a delivery time in ml/hr without regard to volume limit, loading dose or bolus dose), and an intermittent volume-over-time mode (in which the clinician specifies a delivery volume for a specific delivery time, after which the delivery stops for a programmed interval, with the pattern repeating without regard to volume limit, loading dose or bolus dose), to name a few examples.

With respect to the syringe profile libraries 55 and 56, each syringe profile therein contains characterization information (about a respective syringe 16, e.g., physical measurements of the respective syringe 16) and/or identification information that is used by the head processing unit 40 to determine how to operate the stepper motor 58 and piston drive 28 to expel the fluid contents of the syringe 16. For example, a syringe profile may include a model name that specifies the particular model and/or manufacturer of a syringe 16 that is to be used, as well as a specific volume for that syringe 16 and physical measurements associated with the syringe 16. Each syringe profile also includes information that is utilized to display an identification of a syringe 16 (e.g., the manufacturer and model of a syringe 16) on the display 30 of the syringe pump 10 and is further utilized by the syringe pump 10 to calculate and/or determine, during an infusion regimen for example, when the syringe 16 is empty.

To set up an infusion regimen, the clinician will typically load a syringe 16 on the head 12, the processor 40 will cause various menus to appear on display 30, and the clinician (not shown) will select various choices and/or enter various data via the operating interface 32 to select a mode and program the details necessary for a desired infusion regimen. The clinician may also actuate an appropriate switch of the operator interface 32 to initiate the infusion regimen or take other actions before, during, or after the infusion regimen.

The event set identifier 60 may be preset at the factory with a predetermined number, such as zero, then subsequently incremented, decremented, or otherwise adjusted by the at least one head processing unit 40 upon either the initiation or the conclusion of an identifiable event to define the current event set identifier 60. In this manner, the syringe pump 10 includes a first event set identifier 60 with data developed in connection with activity starting with a first identifiable event and also includes a second, different event set identifier 60 with data developed in connection with activity starting with a second identifiable event. By way of example, when the syringe pump 10 is turned on such as by actuation of a switch of the operator interface 32, the event set identifier 60 may be adjusted to thus apply that new event set identifier 60 to the data being collected and/or transmitted by the syringe pump 10 going forward, such as for a preset window of time or until the next identifiable event. By way of further example, when the clinician selects an infusion regimen, such as by beginning the programming steps therefor or confirming the settings thereof, the event set identifier may be adjusted again to create or otherwise define a new event set identifier 60 which will be applied with the data going forward such that the programming activity, syringe pump activity, and related alarms, if any, in regard to that infusion regimen will be associated with the event set identifier 60 as adjusted for that event. It will be appreciated, however, that the first time an infusion regimen is selected after turn-on, the syringe pump 10 could alternatively be programmed to consider that infusion regimen to be part of the same event related to the turn-on event, such that the event set identifier is not adjusted in response to selection of that first infusion regimen or the confirmation of settings thereof such that data for that infusion regimen is associated with the same event set identifier used for the turn-on event.

As another example, the clinician may select a second infusion regimen after a first infusion regimen (either the first after turn-on, or just a first sequentially before a second at some other time during use of the syringe pump 10) has completed or otherwise stopped. In response, the event set identifier 60 may again be adjusted to create yet another new event set identifier 60 which will now be provided with all data going forward such that the programming activity, syringe pump activity, and related alarms, if any, in regard to the second infusion regimen will be associated with the adjusted event set identifier 60. In the above examples, the event set identifier 60 may be adjusted by being incremented, although as an alternative, the event set identifier 60 may be decremented, rather than incremented, upon the initiation of the identifiable event. Alternatively or additionally, the event set identifier 60 may be incremented (or decremented) at the conclusion of an identifiable event, one example of which could be the end of an infusion regimen as detected by processor 40 determining that the volume infused has reach the programmed value, or detecting that the syringe 16 is empty.

Turning to the base 14, the base 14 includes at least one base processing unit 64 coupled to a base memory 66 and a head interface 68 (illustrated as "head I/F" 68) to interface with the base interface 62 of the head 12. Each base processing unit 64 is also typically implemented in hardware using circuit logic disposed in one or more physical integrated circuit devices, or chips. Each base processing unit 64 may also be one or more microprocessors, micro-controllers, field programmable gate arrays, or ASICs, while base memory 66 includes a flash memory 70, and is also typically implemented using circuit logic disposed on one or more physical integrated circuit devices, or chips. It will be appreciated by a person having ordinary skill in the art that base memory 66 may be considered to include memory storage physically located elsewhere in the base 14 (e.g., any cache memory in the at least one base processing unit 64 and any additional memory in the base 14).

The flash memory 70 is configured to store the firmware 72 for the base 14 as well as at least one log 73 that stores data generated by the head 12 and base 14 and a pump information data structure 74. The pump information data structure 74 is configured to store information about the syringe pump 10, such as any or all of an indication of the particular revision of the firmware or configuration data installed on the syringe pump 10, a data structure identifier for the syringe pump 10 that indicates the particular data structure used by the syringe pump 10 to store information, and a component identifier that indicates the particular hardware configuration of the syringe pump 10.

Figure 4:
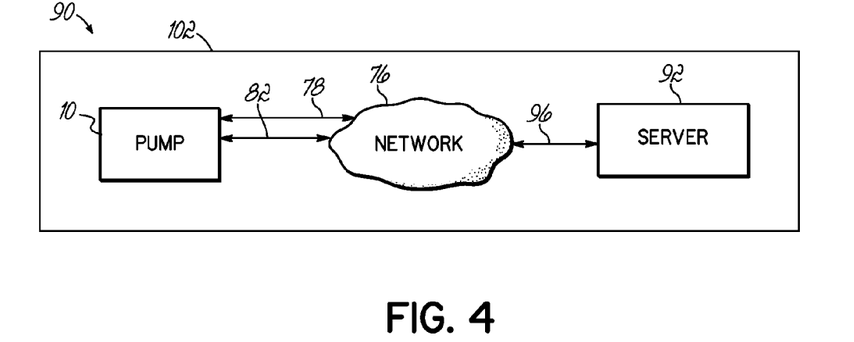
FIG. 4 is a diagram illustrating communicative coupling of the syringe pump of FIG. 1 with an exemplary computing system.

The base 14 is configured to couple to a network 76 through a cable as at 78 with a wired network interface 80 (illustrated as "wired network I/F" 80) coupled to the base processing unit 64. Alternatively, the base 14 may be configured to couple to the network 76 through a wireless signal as at 82 with a wireless network interface 84 (illustrated as "wireless network I/F" 84) coupled to the base processing unit 64. In this manner, the base 14 is configured to communicate across the network 76 to send and receive data, such as to or from a server 92 (FIG. 4). The base 14 also includes power supply circuitry 86 to convert AC power to DC power for the head 12 and base 14 when the base 14 is coupled to an AC power source (not shown), as well as an energy storage device 88 to supply DC power to the head 12 and base 14 when the base 14 is not coupled to the AC power source.

FIG. 4 is a diagrammatic illustration 90 showing an exemplary communicative coupling between the syringe pump 10 and at least one computing system shown here as a server 92. The server 92 is communicatively coupled to the network 76 as at 96 to communicate with the syringe pump 10 over network 76. Thus, syringe pump 10 may receive data from or transmit data to server 92. The syringe pump 10, server 92, and the patient 24 (FIG. 2) coupled to the syringe 16 on syringe pump 10 may be located in a hospital or medical treatment facility 102, although it will be appreciated that server 92 could be a separate facility (not shown). In regard to data transmitted by syringe pump 10, the data advantageously includes an associated event set identifier 60. As a consequence, the data at server 92 can be parsed electronically for data sharing a common event set identifier 60 to locate the data for activity starting with the identifiable event related to that event set identifier 60. In that way, data in regard to activity starting with an identifiable event is interassociated into an identifiable set based on the event set identifier 60. When the data is to be accessed, it can be parsed by or through server 92 so as to collect and/or report a set (or sets) of data interassociated by a common event set identifier 60 for that data (or, as to each set of multiple sets of data, the respective common event set identifier 60 for that set of data).

Figure 5:
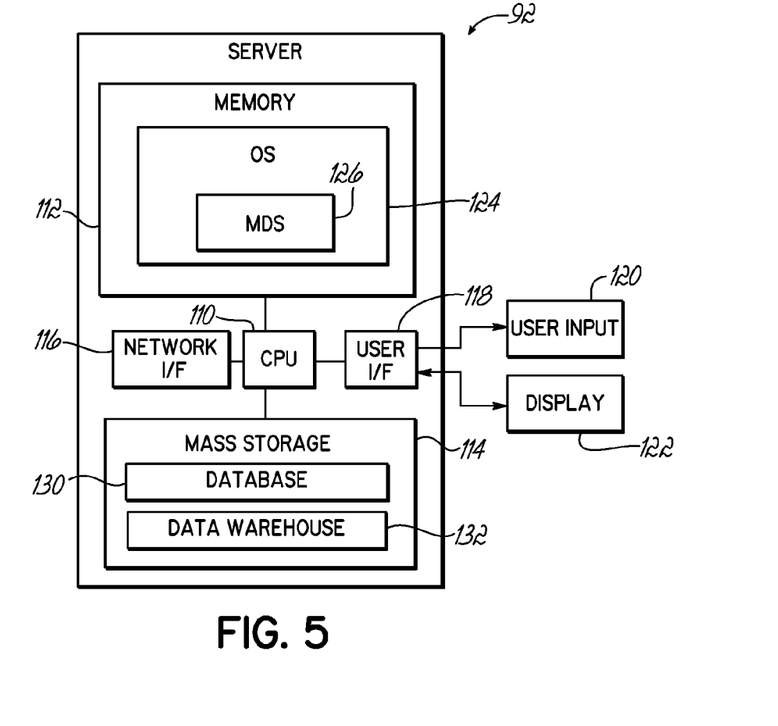
FIG. 5 is a diagrammatic illustration of the hardware and software components of the computing system of FIG. 4.

FIG. 5 is a diagrammatic illustration of the server 92. The server 92 may include at least one computer, computer system, computing device, server, disk array, or programmable device such as a multi-user computer, a single-user computer, a handheld device, a networked device (including a computer in a cluster configuration), etc. The server 92 includes at least one central processing unit ("CPU") 110 coupled to a memory 112. Each CPU 110 is typically implemented in hardware using circuit logic disposed in one or more physical integrated circuit devices, or chips and may be one or more microprocessors, micro-controllers, field programmable gate arrays, or ASICs, while memory 112 may include random access memory (RAM), dynamic random access memory (DRAM), static random access memory (SRAM), flash memory, EEPROM and/or another digital storage medium, and is typically implemented using circuit logic disposed on one or more physical integrated circuit devices, or chips. As such, memory 112 may be considered to include memory storage physically located elsewhere in the server 92, e.g., any cache memory in the at least one CPU 110, as well as any storage capacity used as a virtual memory, e.g., as stored on a mass storage device 114, a computer, or another controller coupled to the server 92 through at least one network interface 116 by way of the network 76 (FIGS. 3 and 4).

The server 92 includes peripheral devices coupled through an input/output device interface 118. As such, the server 92 is configured to receive data from a user through at least one user interface (including, for example, a keyboard, mouse, and/or other user interface) 120 and/or output data to a user through at least one output device (including, for example, a display, speakers, and/or another output device) 122. Alternatively, the input/output device interface 118 communicates with a device that includes a user interface and at least one output device in combination, such as a touchscreen (not shown).

The server 92 is under the control of an operating system 124 and executes or otherwise relies upon various computer software applications, components, programs, files, objects, modules, etc. The server 92 is also configured with a medical device server ("MDS") software component 126 (illustrated as, and referred to hereinafter, as "MDS" 126). The MDS 126 is configured to receive data from the syringe pump 10, determine the validity of the syringe pump 10, determine the validity of data from the syringe pump 10, and store that data in a database 130. As such, the server 92 is configured to store the discrete instances of data from a syringe pump 10 that include the event set identifier 60. The MDS 126 is also configured to respond with an acknowledgment that the MDS 126 has verified and received the data.

As illustrated in FIG. 5, the server 92 is also configured with a data warehouse data structure 132 that provides a static copy of at least a portion of the data in the database 130 and is typically updated once a day. The MDS 126 may be configured to respond to requests from a user of the server 92 and/or a user in communication with the server 92 (e.g., through a separate computing system, which is not shown) to provide data stored by the server 92 in the database 130 and/or data warehouse 132 in the form of a report. Thus, the server 92 can easily parse the data from the syringe pump 10 to locate and access data for one or more event set identifiers 60.

The routines executed to implement the present invention, whether implemented as part of an operating system or a specific application, component, program, object, module or sequence of instructions executed by one or more medical devices 1, such as one or more syringe pumps 10, and one or more remote computers RC, such as one or more servers 92, will be referred to herein as a "sequence of operations," a "program product," or, more simply, "program code." The program code typically comprises one or more instructions that are resident at various times in various memory and storage devices, and that, when read and executed by one or more processors, such as head processing units 40 or base processing units 64 of syringe pump 10, or CPUs 110 of server 92, cause that pump 10 and/or server 92 to perform the steps necessary to execute steps, elements, and/or blocks embodying the various aspects of the invention by thus using the processor(s).

A person having ordinary skill in the art will appreciate that the various aspects of the present invention are capable of being distributed as a program product in a variety of forms, and that the invention applies equally regardless of the particular type of computer readable signal bearing media used to actually carry out the distribution. Examples of computer readable signal bearing media include but are not limited to physical and tangible recordable type media such as volatile and nonvolatile memory devices, floppy and other removable disks, hard disk drives, optical disks (e.g., CD-ROM's, DVD's, etc.), among others, and transmission type media such as digital and analog communication links.

In addition, various program code described hereinafter may be identified based upon the application or software component within which it is implemented. However, it should be appreciated that any particular program nomenclature that follows is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the invention is not limited to the specific organization and allocation of program functionality described herein.

Figure 6:
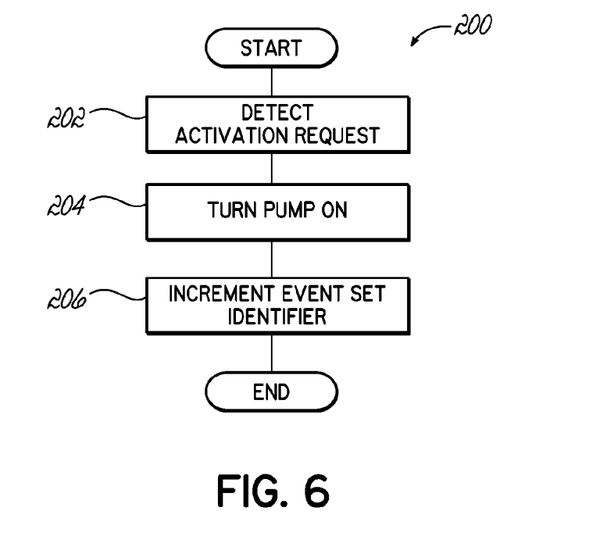
FIG. 6 is a flowchart illustrating an embodiment of a sequence of operations executable by the syringe pump of FIG. 2 to increment an event set identifier to be used to interassociate data in response to the identifiable event being activation of the syringe pump.

The interassociation of data with respect to an identifiable event will now be described by reference to the flowchart 200 of FIG. 6 which illustrates a sequence of operations for the syringe pump 10 to detect an activation request (block 202) and, in response to detecting that activation request, turn on (block 204) and increment the event set identifier 60 (block 206). By way of example, the syringe pump 10 may increment the event set identifier 60 by one in block 206.

Figure 7:
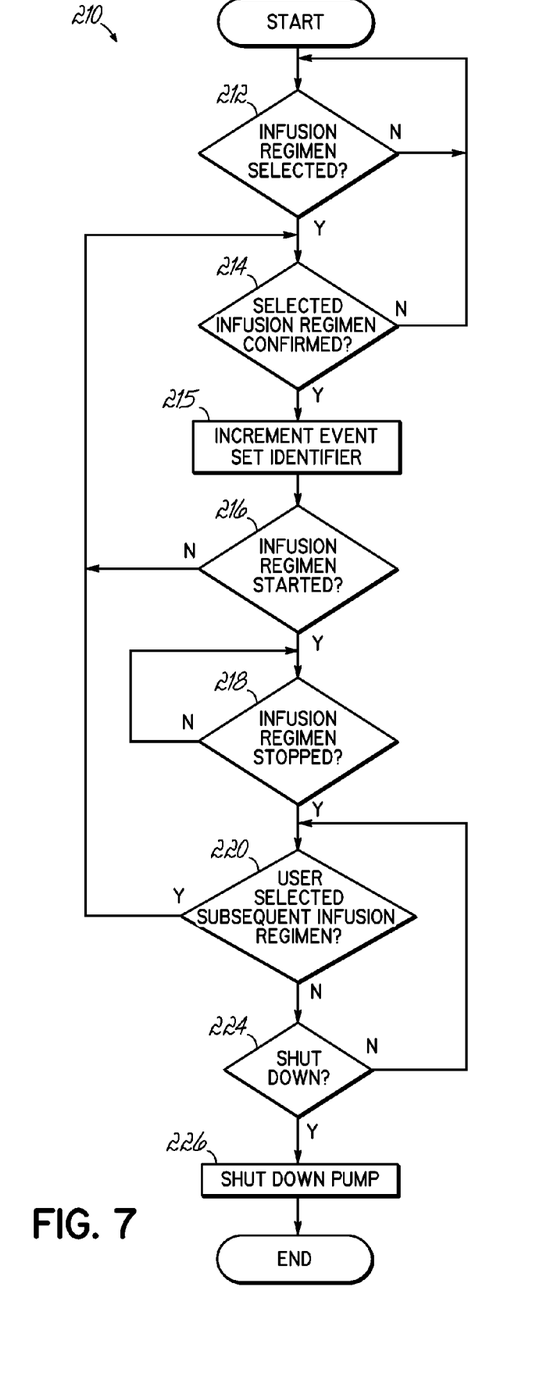
FIG. 7 is a flowchart illustrating an embodiment of a sequence of operations executable by the syringe pump of FIG. 2 to increment the event set identifier to be used to interassociate data in response to the identifiable event being confirmation of an infusion regimen to be performed by the syringe pump.

With reference to flowchart 210 of FIG. 7, the syringe pump 10 monitors clinician input, such as from operator interface 32 to determine whether the clinician has selected an infusion regimen (block 212). When the clinician has not selected an infusion regimen ("No" branch of decision block 212), which may occur while the syringe pump 10 is sitting idle or the clinician is undertaking other activities such as adjustments to settings associated with the syringe pump 10, the sequence of operations returns back to block 212. However, when the clinician has selected an infusion regimen ("Yes" branch of decision block 212), the syringe pump 10 determines whether the clinician has confirmed the settings for the infusion regimen (e.g., the clinician has adjusted settings for the infusion regimen or otherwise chosen not to adjust settings for the infusion regimen) (block 214). In response to determining that the clinician has not confirmed the settings for the infusion regimen ("No" branch of decision block 214), the sequence of operations returns back to block 212. However, when the clinician has confirmed the settings for the infusion regimen ("Yes" branch of decision block 214), the syringe pump 10 increments the event set identifier 60 (block 215) and determines whether the infusion regimen has been started (block 216). By way of example, the syringe pump 10 may increment the event set identifier 60 by one in block 215. When the infusion regimen has not been started ("No" branch of decision block 216), the sequence of operations returns to block 214 to again determine whether the clinician has decided to confirm the settings of the infusion regimen.

When the infusion regimen has been started ("Yes" branch of decision block 216), the pump determines if the infusion regimen has been stopped (e.g., in response to being paused, canceled, or completed) (block 218). When the infusion regimen has not been stopped ("No" branch of decision block 218), the sequence of operations returns back to block 218. However, when the infusion regimen has been stopped (e.g., such as when the infusion regimen has completed or been canceled) ("Yes" branch of decision block 218), the syringe pump 10 determines whether the clinician has selected a subsequent or second infusion regimen (block 220). By way of example, the syringe pump 10 may determine whether the clinician has navigated back to a screen or menu on display 30 of the syringe pump 10 so as to program a new infusion regimen. If the clinician has selected a subsequent infusion regimen ("Yes" branch of decision block 220), the sequence of operations returns back to block 214. When the clinician has not selected a subsequent infusion regimen ("No" branch of decision block 220), the syringe pump 10 determines whether the clinician has selected to shut down the pump (block 224). If the clinician has not selected to shut down the pump ("No" branch of decision block 224), the clinician may later decide to select a new infusion regimen, so the sequence of operations returns to block 220. However, when the clinician has selected to shut down the pump ("Yes" branch of decision block 224), the pump shuts down (block 226) and the sequence of operations ends. There may be a situation between block 218 and block 220 in which an infusion regimen stops but is subsequently continued without starting a new infusion regimen, such as when the infusion regimen stops due an occlusion alarm that is subsequently addressed. As such, the sequence of operations for the syringe pump 10 in that situation may loop back to block 218 rather than continue to block 220.

Thus, flowcharts 200 and 210 illustrate that the event set identifier 60 is incremented when an infusion regimen has been confirmed by the clinician and/or after the clinician has turned on a deactivated syringe pump 10. In some applications, the clinician may cause the syringe pump to conduct an infusion regimen with a medicament, followed by an infusion regimen with a flushing solution to clear the fluid line 26. The syringe pump 10 may be programmed to treat both infusion regimens as one identifiable event, such that the event set identifier 60 is not adjusted upon selection of the infusion regimen for flushing the fluid line 26. The data for both infusion regimens will thus be interassociated by the same event set identifier 60.

Additionally or alternatively, the syringe pump 10 may advantageously adjust the event set identifier 60 in response to the clinician selecting any infusion regimen or starting any infusion regimen. As such, the syringe pump 10 may increment the event set identifier 60 when the clinician selects or starts an infusion regimen whether or not the clinician confirms the settings thereof. Moreover, the event set identifier 60 need not be adjusted when the clinician selects, starts, or confirms a first infusion regimen after activation of the syringe pump 10, and instead may be adjusted when the clinician selects or confirms a second infusion regimen, even if it is for flushing the fluid line 26, after the first infusion regimen has stopped. Furthermore, the syringe pump 10 may advantageously adjust the event set identifier 60 in response to an infusion regimen proceeding from one procedure to another procedure within that same infusion regimen. As such, the syringe pump 10 may increment the event set identifier 60 when the clinician selects an infusion regimen after activation of the syringe pump 10 as well as when the infusion regimen proceeds from a first procedure thereof to a second procedure thereof.

Figure 8:
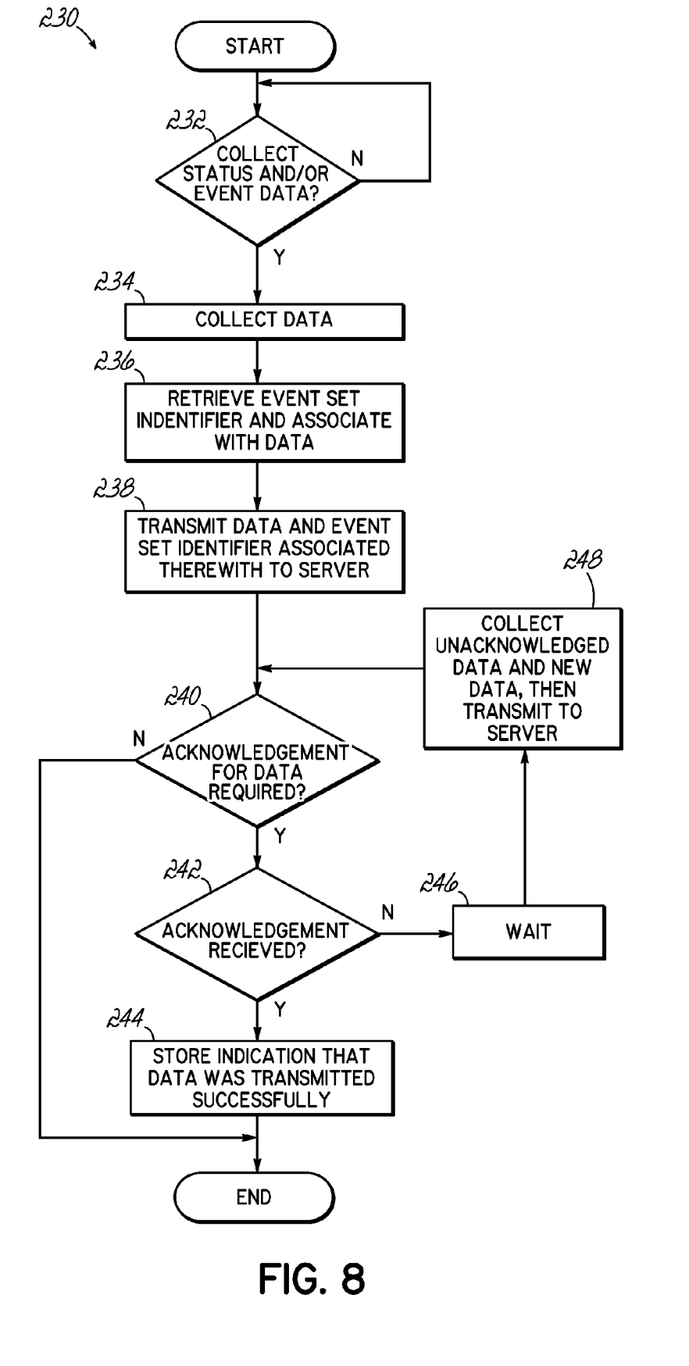
FIG. 8 is a flowchart illustrating a sequence of operations executable by the syringe pump of FIG. 2 to associate an event set identifier with data in regard to an identifiable event of the syringe pump and transmit same to the computing system of FIG. 4.

With reference to flowchart 230 of FIG. 8, this sequence of operations illustrates that the syringe pump 10 collects and transmits data that is associated with an event set identifier 60. The head 12 of the syringe pump 10 monitors for status and/or event data (block 232) and, when it detects that it is supposed to collect that data ("Yes" branch of decision block 232), the head 12 collects at least one instance of data (e.g., at least one discrete instance of data associated with the activity, such as status or event) (block 234). By way of example, the head 12 of the syringe pump 10 is configured to collect data associated with the operation, i.e., activity, of the syringe pump 10 at the following designated points in the head's work flow: after the syringe pump 10 has started up, at the selection of a drug program, at the end of a procedure of an infusion regimen, at the end of an infusion regimen, at a change of any portion of the infusion regimen, at an alarm, at the clearing of an alarm, when the syringe pump 10 is powered on, before the syringe pump 10 is powered down, at a calibration of the syringe pump 10, in response to an indication that maintenance is required, and at other clinician actions (such as interaction with the operator interface 32 of the head 12 to override a data value). The head 12 or the base 14 of the syringe pump 10 may also be configured to collect data at start-up, at the first start-up for the day, and at predetermined intervals when the syringe pump 10 is turned on. When data is collected, it is time-stamped with a time tracked by the syringe pump 10. Some of this data represents status data (e.g., status data may include an indication of the power source of the syringe pump 10, the level of its energy storage device 88, and the settings for an infusion regimen), while other data represents event data (e.g., event data may include alarm, fault, maintenance, therapy, therapy change, telemetry, and power events). Periodically, the base 14 of the syringe pump 10 queries the head 12 of the pump for data. If the head 12 is not busy, it replies with the data. If the head 12 is busy, the base 14 waits and queries the head 12 of the syringe pump 10 for data again. Upon receiving data from the head 12, the base 15 may store the data in its log 73 with an indication that the data has not been transmitted, prepares unsent data to be transmitted to the server 92, and causes that unsent data to be transmitted such as over network 76 to server 92. Alternatively, the syringe pump 10 may immediately prepare and transmit the data.

In any event, after, or in connection with, collecting data (block 234), the syringe pump 10 also retrieves the event set identifier 60 and associates it with the collected gathered data (block 236). The syringe pump 10 transmits the collected data and its associated event set identifier 60 to the server 92 (block 238). In response to that transmission, the syringe pump 10 determines whether an acknowledgment for that data is necessary (block 240). For example, the syringe pump 10 may be configured to track what data is received, validated, and/or stored by the server 92. Alternatively, the data may be transmitted without a need for acknowledgement that it has been received, validated, and/or stored by the server 92. As such, when an acknowledgement for the transmitted data is not necessary ("No" branch of decision block 240), the sequence of operations may end.

However, when an acknowledgement for transmitted data is required ("Yes" branch of decision block 240), the syringe pump 10 determines whether an acknowledgment from the server 92 has been received (block 242). When the base 14 receives an acknowledgment from the server 92 that the transmitted data has been successfully received, validated, and/or stored ("Yes" branch of decision block 242), the base 14 indicates in its log 73 that the data associated with that acknowledgment was successfully transmitted (block 244) and the sequence of operations may end. Thus, data for which acknowledgement has been received will not be transmitted to the server 92 again. When the base 14 has not received an acknowledgment from the server 92 ("No" branch of decision block 242), it waits for a period of time, such as one to two minutes (block 246), and collects and transmits both the previously unacknowledged data as well as new, as yet untransmitted, data (block 248) and returns back to block 240. In block 240, the syringe pump 10 again determines, for each set of data, whether each instance of data requires an acknowledgement and proceeds, for each instance, as described above.

When the server 92 receives data from the syringe pump 10, it may determine if the data is corrupted or from a device that is not recognized by the server 92. If the data is corrupted or from an unrecognized device, the server 92 quarantines the data for future analysis. When the server 92 receives data from the syringe pump 10 and is able to verify that the data is uncorrupted and from a recognized pump 10, the server 92 stores the data. The server 92 may also send an acknowledgment that the data from the syringe pump 10 has been received when it is able to store the data therefrom successfully.

The server 92 is also configured to provide reports to clinicians and/or technicians (both not shown) based on data from the various medical devices, such as syringe pumps 10 from which server 92 receives data. By way of example, a clinician may request data for a particular syringe pump 10 via a terminal (not shown) coupled to the server directly or via the network 76. The server 92 accesses the data in its data warehouse 132 and reports out the data for the identified syringe pump 10. To facilitate review by the clinician, the data may be grouped as interassociated by respective event set identifiers 60, such that the clinician may be provided a report of sets of the data grouped by identifiable events, or as a single set for a specified event.

The server 92 may provide reports in response to a request from another computing system (not shown) for a specific syringe pump 10 and/or with respect to a specific event set identifier 60. The server 92 acts upon the request by accessing the stored data associated with that request. By way of example, the server 92 may initially locate the data associated with the syringe pump 10, filter that located data to preclude accessing unwanted data, then access the data specified by the request. Such access includes accessing data associated with activity starting with a first event set identifier 60 but not a second, different event set identifier 60. The report is then generated form that accessed data.

The server 92 may be in communication with a plurality of pumps 10 and reports may include information from the data warehouse 132 of the server 92 that is, in turn, associated with the plurality of pumps 10. Specifically, the reports may include data associated with the plurality of pumps 10 as well as respective event set identifiers 60 that interassociate respective discrete instances of that data from particular pumps 10. In this manner, the data in the data warehouse 132 may be searchable, filterable, or otherwise sortable to access data associated with not only a particular syringe pump 10, but also a particular event set identifier 60 or group of event set identifiers 60 associated with that particular syringe pump 10.

The report(s) will reflect the data, as processed or otherwise manipulated consistent with any filtering requested by the clinician and/or included in data warehousing of the data, and may or may not specify the event set identifier 60 and/or the particular identifiable event in the report(s). But the server 92 is thus able to group data for activity starting with identifiable events without devoting time or resources to parsing the data based on start and stop times, such as would require review of large blocks of data and the time-stamps of each instance of data in order to locate the data of interest. Instead, the event set identifier can be used to access a set or sets of data associated with activity starting with an identifiable event or events.

By virtue of the foregoing, there is thus provided a mechanism for simply and automatically parsing data from a medical device in accordance with identifiable events of the device.

While the present invention has been illustrated by a description of embodiments thereof, and the embodiments have been described in considerable detail, it is not the intention of the applicants to restrict or in any way limit the scope of the appended claims to such detail. Additional advantages and modifications will readily appear to those having ordinary skill in the art. To that end, while an exemplary syringe pump 10 and its operation were set forth in detail in FIGS. 2 though 8, one of ordinary skill in the art will appreciate that the event set identifier feature of the present invention may be applied to other medical devices referenced generically as medical device 1 in FIG. 1 used in the treatment, diagnosis, or care of patients, examples of which are other types of medical pumps (e.g., IV pumps, LVP pumps, peristaltic pumps, and implantable pumps) or medical monitoring devices (e.g. blood pressure monitors, heart monitors, and pulse oximeters). As will be readily appreciated by one of ordinary skill in the art, the identifiable events for which an adjustment may be made in the event set identifier 60 will be specified for the nature and type of the medical device 1 and the type or groupings of data that may be desired. As an example, while one identifiable event for the syringe pump 10 is the selection or confirmation of an infusion regimen, an identifiable event for another medical device 1 may be the selection of a monitoring session or procedure. Also, other alternative hardware and/or software environments may be used than those shown herein. Similarly, a person having ordinary skill in the art will appreciate that any of the blocks of the above flowcharts may be deleted, augmented, made to be simultaneous with another, combined, or be otherwise altered in accordance with the specific needs of the medical device 1 and the patient or facility needs in the use of that medical device 1. By way of example, the flowcharts describe incrementing the event set identifier 60 by one in response to the initiation or conclusion of an identifiable event. Alternative methods of adjusting the event set identifier 60 may be implemented. As such, the event set identifier 60 may be incremented by more than one or decremented by one or more. Alternatively, the event set identifier 60 may include multiple fields that each provide information about the event. By way of further example, a first field of the event set identifier 60 may indicate the particular type of identifiable event, while a second field of the event set identifier 60 may indicate how many times that particular type of identifiable event has been selected or detected. The invention in its broader aspects is therefore not limited to the specific details, representative apparatus and method, and illustrative example shown and described. Further, access may be had to at least the first identifiable event and/or at least the second identifiable event by parsing the data for the first and/or second event set identifier 60 associated therewith. Accordingly, departures may be made from such details without departing from the spirit or scope of the general inventive concept.

Having described the invention, what is claimed is:

1. A method of interassociating data of a medical device, comprising:
   using a processor to define, for each occurrence of an identifiable event of a plurality of identifiable events of the medical device, a representative event set identifier, such that a plurality of different event set identifiers are each associated with respective identifiable events of the plurality of identifiable events; and
   associating, with data collected in connection with activity of the medical device occurring over time and starting with a respective identifiable event until a subsequent identifiable event, the event set identifier associated with the respective identifiable event, such that data collected for the activities occurring between a first and a second identifiable event are interassociated with a respective first event set identifier for the first identifiable event, data collected for the activities occurring between the second and a third identifiable event are interassociated with a respective second event set identifier for the second identifiable event, and the data can be parsed into a set of data for activity occurring between the respective and subsequent identifiable events of the medical device based upon the associated event set identifier for the respective identifiable event.

2. The method of claim 1 further comprising using the processor to include the second, different event set identifier with the data collected for the activities occurring between the second and the third identifiable events of the medical device.

3. The method of claim 1 further comprising activating the medical device, the activation being the first identifiable event.

4. The method of claim 1 further comprising deactivating the medical device, the deactivation being the first identifiable event.

5. The method of claim 1, wherein the medical device is a medical pump, the method further comprising selecting a first infusion regimen, the selection of the first infusion regimen being the first identifiable event.

6. The method of claim 5 further comprising selecting a second infusion regimen after the first infusion regimen has been stopped, the selection of the second infusion regimen being the second identifiable event.

7. The method of claim 1 further comprising adjusting the first event set identifier to define the second, different event set identifier in response to detecting the second identifiable event.

8. The method of claim 7, adjusting the first event set identifier including incrementing the first event set identifier.

9. The method of claim 7, adjusting the first event set identifier including decrementing the first event set identifier.

10. The method of claim 1 further comprising transmitting the data collected for the activities occurring between the first and the second identifiable events along with the first event set identifier to a computing system.

11. The method of claim 10 further comprising accessing, through the computing system, the data collected for the activities occurring between the first and the second identifiable events by parsing the data for the first event set identifier.

12. The method of claim 10 further comprising transmitting data collected for the activities occurring between the second and the third identifiable events along with the second event set identifier to the computing system.

13. The method of claim 12 further comprising accessing, through the computing system, the data collected for the activities occurring between the second and the third identifiable events by parsing the data for the second event set identifier.

14. The method of claim 1 further comprising accessing the data collected for the activities occurring between the first and the second identifiable events by parsing the data for the first event set identifier.

15. The method of claim 1 further comprising accessing the data collected for the activities occurring between the second and the third identifiable events by parsing the data for the second event set identifier.

16. A method of interassociating data of a medical device, comprising:
   including a first event set identifier with data developed in connection with activity of the medical device occurring over time and starting with a first identifiable event until a subsequent second identifiable event of the medical device; and
   using a processor to include a second, different event set identifier with data developed in connection with activity of the medical device occurring over time and starting with the second identifiable event until a subsequent third identifiable event of the medical device, such that the data collected for the activities occurring between the first and the second identifiable events is interassociated into a first identifiable set by the first event set identifier, data collected for the activities occurring between the second and the third identifiable event is interassociated into a second identifiable set by the second event set identifier, and the data can be parsed into the respective set of data for activity occurring between the first and second identifiable events or between the second and third identifiable events of the medical device based upon the associated event set identifier for the first or second identifiable event, respectively.

17. The method of claim 16 further comprising activating the medical device, the activation being the first identifiable event.

18. The method of claim 16 further comprising deactivating the medical device, the deactivation being the first identifiable event.

19. The method of claim 16, wherein the medical device is a medical pump, the method further comprising selecting a first infusion regimen, the selection of the first infusion regimen being the first identifiable event.

20. The method of claim 19 further comprising selecting a second infusion regimen after the first infusion regimen has been stopped, the selection of the second infusion regimen being the second identifiable event.

21. The method of claim 16 further comprising adjusting the first event set identifier to define the second, different event set identifier in response to detecting the second identifiable event.

22. The method of claim 21, adjusting the first event set identifier including incrementing the first event set identifier.

23. The method of claim 21, adjusting the first event set identifier including decrementing the first event set identifier.

24. The method of claim 16 further comprising transmitting the data developed in connection with activity of the medical device occurring over time and starting with the first identifiable event until the subsequent second identifiable event of the medical device along with the first event set identifier to a computing system.

25. The method of claim 24 further comprising accessing, through the computing system, the data developed in connection with activity of the medical device occurring over time and starting with the first identifiable event until the subsequent second identifiable event of the medical device by parsing the data for the first event set identifier.

26. The method of claim 24 further comprising transmitting data developed in connection with activity of the medical device occurring over time and starting with the second identifiable event until the subsequent third identifiable event of the medical device along with the second event set identifier to the computing system.

27. The method of claim 26 further comprising accessing, through the computing system, the data developed in connection with activity of the medical device occurring over time and starting with the second identifiable event until the subsequent third identifiable event of the medical device by parsing the data for the second event set identifier.

28. The method of claim 16 further comprising accessing the data developed in connection with activity of the medical device occurring over time and starting with the first identifiable event until the subsequent second identifiable event of the medical device by parsing the data for the first event set identifier.

29. The method of claim 16 further comprising accessing the data developed in connection with activity of the medical device occurring over time and starting with the second identifiable event until the subsequent third identifiable event of the medical device by parsing the data for the second event set identifier.

30. A medical device, comprising:
at least one processing unit; and
a memory, the memory containing program code being configured to be executed by the at least one processing unit to define, for each occurrence of an identifiable event of a plurality of identifiable events of the medical device, a representative event set identifier, such that a plurality of different event set identifiers are each associated with respective identifiable events of the plurality of identifiable events, and to associate with data collected in connection with activity of the medical device occurring over time and starting with a respective identifiable event until a subsequent identifiable event, the event set identifier associated with the respective identifiable event, such that data collected for the activities occurring between a first and a second identifiable event are interassociated with a respective first event set identifier for the first identifiable event, data collected for the activities occurring between the second and a third identifiable event are interassociated with a respective second event set identifier for the second identifiable event, and the data can be parsed into a set of data for activity occurring between the respective and subsequent identifiable events of the medical device based upon the associated event set identifier for the respective identifiable event.

31. The medical device of claim 30, the program code being further configured to define activation of the medical device as the first identifiable event.

32. The medical device of claim 30, the program code being further configured to define deactivation of the medical device as the first identifiable event.

33. The medical device of claim 30 being a medical pump, the program code being further configured to define selection of a first infusion regimen as the first identifiable event.

34. The medical device of claim 33, the program code being further configured to define selection of a second infusion regimen after the first infusion regimen has been stopped as the second identifiable event.

35. The medical device of claim 30, the program code being further configured to adjust the first event set identifier to define the second, different event set identifier in response to detecting the second identifiable event.

36. The medical device of claim 35, the program code being further configured to adjust the first event set identifier by incrementing the value thereof.

37. The medical device of claim 35, the program code being further configured to adjust the first event set identifier by decrementing the value thereof.

38. The medical device of claim 30, the program code being further configured to transmit the data collected for the activities occurring between the first and the second identifiable events, and the activities occurring between the second and the third identifiable events along with the associated first and second event set identifiers to a computing system.

39. A method of interassociating data of a medical device adapted to collect data and transmit the data to a computing system, wherein the data collected and transmitted by the medical device includes a respective event set identifier associated with data developed in connection with activity of the medical device occurring over time and starting with a respective identifiable event until a subsequent identifiable event, the method comprising:
receiving at the computing system data and an associated event set identifier in connection with activity of the medical device occurring over time and starting with the respective identifiable event until the subsequent identifiable event, the event set identifier associated with the respective identifiable event, such that data collected for the activities occurring between a first and a second identifiable event are interassociated with a respective first event set identifier for the first identifiable event, and data collected for the activities occurring between the second and a third identifiable event are interassociated with a respective second event set identifier for the second identifiable event; and
parsing the data into a set of data for activity occurring over time and starting with the respective identifiable event until the subsequent identifiable event of the medical device based upon the associated event set identifier for the respective identifiable event.

40. The method of claim 39 further comprising parsing the data into sets of data for a group of identifiable events of the medical device based upon the associated event set identifier for each identifiable event of the group of identifiable events.

41. A computing system for receiving data collected and transmitted by a medical device, the computing system comprising:
at least one processing unit; and a memory containing program code being configured to be executed by the at least one processing unit to:

receive at the computing system the data and an associated event set identifier in connection with activity of the medical device occurring over time and starting with a respective identifiable event until a subsequent identifiable event, such that data collected for the activities occurring between a first and a second identifiable event are interassociated with a respective first event set identifier for the first identifiable event, and data collected for the activities occurring between the second and a third identifiable event are interassociated with a respective second event set identifier for the second identifiable event; and parse the data into a set of data for activity of the medical device occurring over time and starting with one respective identifiable event of the first and second identifiable events until the associated subsequent identifiable event of the medical device based upon the associated event set identifier for that one respective identifiable event.

42. The computing system of claim 41, the program code being further configured to parse the data into sets of data for a group of respective identifiable events of the medical device based upon the associated event set identifier for each respective identifiable event of the group of respective identifiable events.

* * * * *